United States Patent [19]
Field et al.

[11] Patent Number: 5,609,646
[45] Date of Patent: Mar. 11, 1997

[54] ACETABULAR CUP FOR A TOTAL HIP PROSTHESIS

[75] Inventors: Richard E. Field, London, England; Peter Nuijten, County Limerick, Ireland; Neil Rushton, Cambridge, England

[73] Assignee: Howmedica International, Shannon, Ireland

[21] Appl. No.: 296,580

[22] Filed: Aug. 26, 1994

Related U.S. Application Data

[63] Continuation-in-part of Ser. No. 3,164, Jan. 12, 1993, abandoned.

[30] Foreign Application Priority Data

Jan. 23, 1992 [GB] United Kingdom .................. 9201477

[51] Int. Cl.$^6$ .................................................. A61F 2/34
[52] U.S. Cl. ................................. 623/22; 623/18
[58] Field of Search ................... 623/16, 18, 20, 623/21, 22, 23

[56] References Cited

U.S. PATENT DOCUMENTS

| | | | |
|---|---|---|---|
| 2,910,978 | 11/1959 | Urist ........................................ | 128/92 |
| 3,707,006 | 12/1972 | Bokros et al. ........................... | 623/16 |
| 4,123,806 | 11/1978 | Amstutz .................................. | 623/22 |
| 4,126,924 | 11/1978 | Akins et al. ............................. | 623/16 |
| 4,166,292 | 9/1979 | Bokros .................................... | 623/16 |
| 4,747,990 | 5/1988 | Gaussens et al. ........................ | 623/22 |

FOREIGN PATENT DOCUMENTS

| | | |
|---|---|---|
| 0051729 | 5/1982 | European Pat. Off. . |
| 0187881 | 7/1986 | European Pat. Off. . |
| 0331622 | 9/1989 | European Pat. Off. . |
| 0388745 | 9/1990 | European Pat. Off. . |
| 2361861 | 3/1978 | France . |
| 2598908 | 11/1987 | France . |
| 2651675 | 3/1991 | France . |
| 2653659 | 5/1991 | France . |

*Primary Examiner*—David Isabella
*Attorney, Agent, or Firm*—Peter C. Richardson; Lawrence C. Akers; Raymond W. Augustin

[57] ABSTRACT

An acetabular cup for a total hip prosthesis has an outer shell and an inner bearing component. The shell is molded around the inner bearing component and has an elastic modulus similar to subchondral bone of between 5 GPa and 18 GPa. The shell has a part-spherical main portion and two independent arms projecting from the part-spherical main portion. The arms are separated from each other by an opening of predetermined shape and size.

12 Claims, 5 Drawing Sheets

5,609,646

ACETABULAR CUP FOR A TOTAL HIP PROSTHESIS

This application is a continuation-in-part of U.S. Ser. No. 08/003,164 filed Jan. 12, 1993 now abandoned.

BACKGROUND OF THE INVENTION

1. Field of the Invention

This invention relates to an acetabular cup for a total hip prosthesis and total hip prostheses embodying such cups. More particularly, the invention relates to a cup having an outer shell designed to exhibit similar flexibility to the load bearing subchondral plate of the natural acetabulum and shaped to allow better load transfer characteristics.

2. Description of the Prior Art

In the mid 1970's total hip replacement designs were made which were classified as double cup arthroplasties. In these the femoral components had no intramedullary stem, but used a relatively thin part-spherical shell which was placed over the top of the femur from which a minimum of bone was removed. Inevitably, the bearing surface for such a design was large, approximating the normal anatomy. The acetabular component bearing surface also had to be large and there was little opportunity to remove a significant quantity of bone from the acetabulum. The acetabular cups for such designs therefore have thin wall thicknesses and are inherently flexible. At the period of development of these designs, almost all acetabular cups were cemented into position and these thin walled flexible acetabular cups flexed too much, thereby causing cracks which progressed around the bone's cement mantle or through it, leading ultimately to a loose acetabular implant. Furthermore, there tends to be elastic movement in the acetabulum, which causes distortion or deformation under load.

Typical examples of such total hips are shown in U.S. Pat. No. 4,123,806 and French Patent Application 2 361 861 (76 25215).

An analysis of the acetabulum in the human pelvis in the load bearing area shows that the load from the femur is transmitted and passes in a relatively direct line from that area up to the sacrum. The load is transmitted via a bar of trabeculae or a column of trabecular bone which is substantially straight so that in an x-ray of a human standing, it can be seen that there is a direct continuation of the medial compressive system of the proximal femur. It is therefore desirable that this area of the acetabulum is loaded and the remainder of the acetabulum should not have any load transmitted to the underlying bowl-shaped surface. A cup having an articular surface beyond the load bearing area, which area is substantially horse-shoe shaped, can only be justified if for some reason the articulation should be greater for the stability of the femoral head. This means that with a large headed hip prosthesis, the surface area of contact can be reduced to levels closer to that of a current conventional stem head cup arthroplasty.

A cup having a horse-shoe shaped opening formed in the shell is shown in U.S. Pat. No. 2,919,978 dated Nov. 3, 1959 and EPO Application 0 051 729 filed Sep. 19, 1981.

The present invention therefore is intended to provide a construction for an acetabular cup for acetabulum surface replacement which can be thin walled, and which has the ability to flex in harmony with bone movements without this leading to loosening of the implant (bone cements in use at present are not well suited to accommodate these movements, but it is possible that more flexible materials may be found in the future). At the same time, this cup is intended to provide a surface area of contact for a large headed hip prosthesis close to that of a current conventional stem head cup arthroplasty.

The present invention is intended to provide an acetabular cup which can be used for large hip head bearing surface diameters and which can also be used for smaller bearing surfaces of more conventional diameters, for example, 28 mm and 32 mm.

SUMMARY OF THE INVENTION

It is an object of the invention to provide a prosthetic acetabular component which flexes in harmony with the natural acetabulum in a manner which minimizes the relative movement between the prosthetic component and the adjacent bone.

The acetabular cup for a total hip prosthesis of the present invention has an outer reinforcing backing and an inner bearing component. The backing has a part-spherical main portion and two independent arms projecting therefrom which are split apart from each other. The arms can be closely adjacent each other, but are preferably spaced apart to provide a gap or opening between them. The independence of the arms allows flexing of the cup which can thus accommodate deformation of the acetabulum.

Preferably the arms are spaced apart or split from each other about an arc on the part-spherical main portion breaking out on the rim, and the arms and the main portion can together be substantially part-spherical. In a convenient construction the backing may comprise a substantially part-spherical wall having a rim which is interrupted by a shaped opening to provide the two spaced apart arms. The opening can take various shapes and may, for example, be semicircular.

The opening can have a mouth which provides the interruption in the rim, said mouth being of smaller width than the remainder of the opening. With this arrangement the backing can be substantially horse-shoe shaped.

For use without a cement mantle, the backing preferably has means for locating it in an acetabulum with which it is to be used, and these may include outwardly extending projections or spikes which can be provided on the backing itself or can be provided on the inner bearing component and extend through apertures in the backing. Preferably the liner and/or the backing are provided with holes in the arms to receive elongate locating means, which can be screws or pins.

As mentioned above, the backing is intended to flex in harmony with the natural acetabular deformation in the pelvis of the user in a manner which minimizes the relative movement between the prosthetic component and the adjacent bone. Therefore the material of the backing is chosen to be of similar stiffness to the subchondral bone it replaces. The inner bearing component can be less stiff than the backing, and in a preferred construction the inner bearing surface of the bearing component is substantially part-spherical over a portion thereof spaced diametrically opposite the split or opening between the arms of the backing when located therein, and is relieved over its remaining inner bearing surface.

The bearing component can take various forms, for example, it can have independent arms similar to the backing with a split or opening between them and can be of substantially the same configuration as the backing, or it can be substantially hemispherical and extend across the split or opening between the arms of the backing. The backing can be made of any suitable material with an elastic modulus of between 5 GPa and 18 GPa, which can be molded around or bonded to the inner bearing component and be rigidly secured to the inner bearing component by mechanical interlock or by adhesion. The invention also includes a total hip prosthesis including a femoral stem and an acetabular cup as set forth above.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENTS

Figure 1:
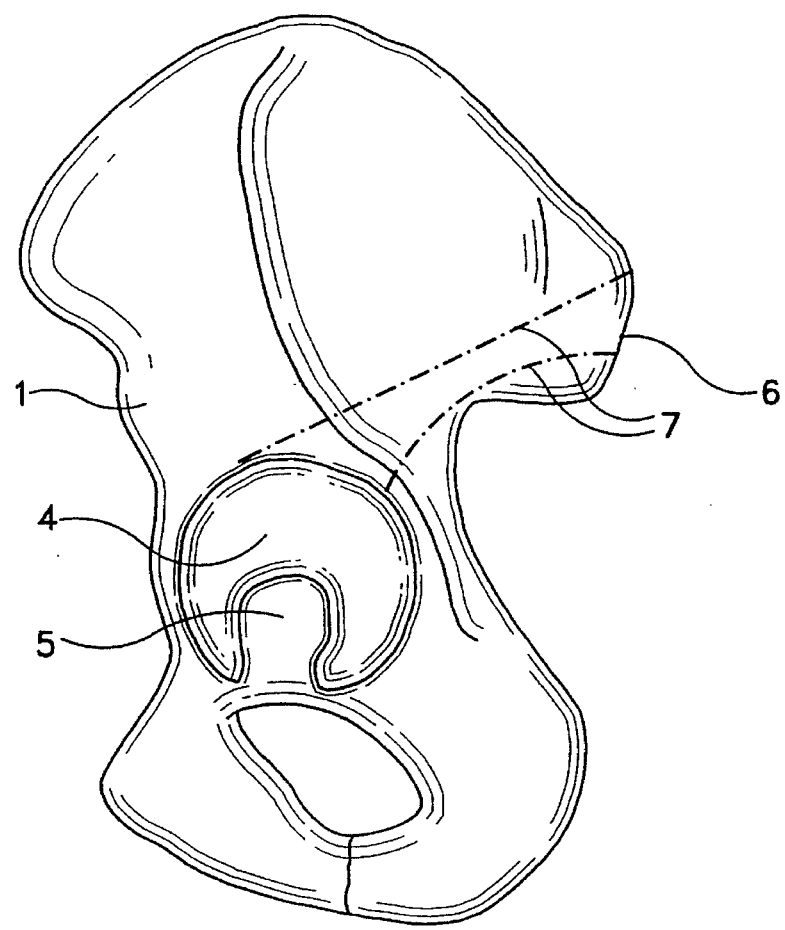
FIG. 1 is a diagrammatic view of part of a human pelvis.

FIG. 1 is a diagrammatic view of half of a human pelvis or ilium I showing the acetabulum 4. Deformation of the acetabulum 4 occurs during walking and hip joint loading. Acetabulum 4 is roughly a horse-shoe shaped cup with a depressed portion which constitutes the foveal recess 5. The articulation with the spine (the sacroiliac joint) is indicated at 6. The main column of support which transfers loads from acetabulum 4 through ilium 1 up to sacroiliac (spinal) joint 6 is indicated by broken lines 7.

Figure 2:
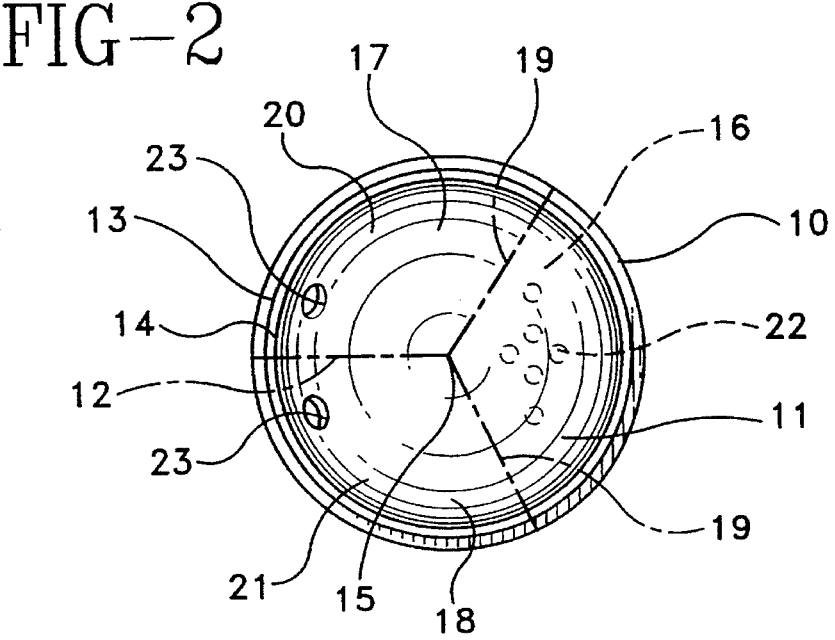
FIG. 2 is a plan view from below of an acetabular cup according to the invention.
Figure 3:
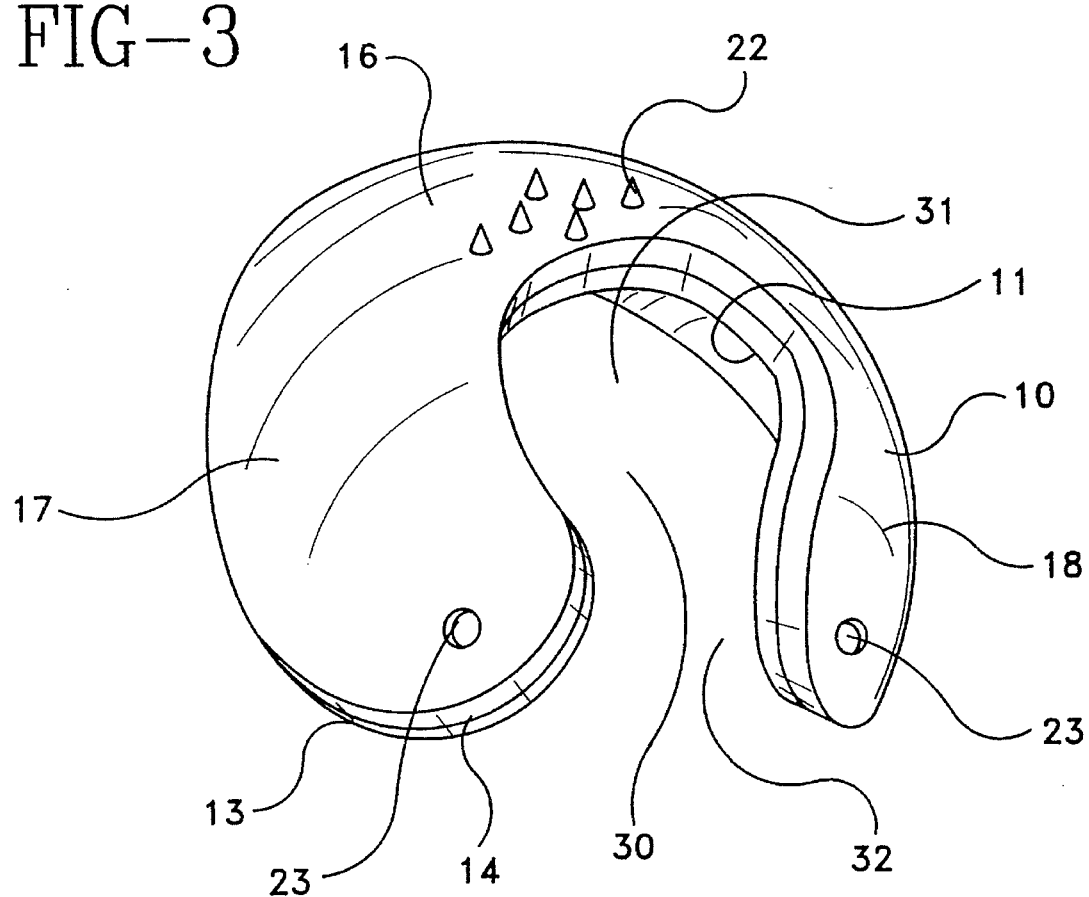
FIG. 3 is an isometric view of an alternate cup construction.

FIG. 2 is a plan view of an acetabular cup according to the present invention which comprises an outer reinforcing backing or shell 10 which is substantially hemispherical and an inner bearing component 11 of substantially the same shape and which fits within backing 10. The backing can be made of any suitable material of similar elastic modulus to subchondral-bone and capable of being molded around the material of the inner bearing component, for example, a carbon fiber reinforced plastics material. The inner bearing component can be made from a suitable bearing material such as ultra-high molecular weight polyethylene.

In the preferred embodiment the backing is comprised of 30% chopped carbon fiber reinforced polybutyleneterephthalate (PBT), with reinforcing fibers of 6.8 to 7.2 μm in diameter. The backing is nominally 1.5 mm thick and is formed by injection molding around a hemispherical blank of ultra-high molecular weight polyethylene, with dovetail projections formed on the blank to provide a mechanical interlock with the backing. The inner bearing component is subsequently formed by machining the bearing surface from the blank, leaving an inner bearing component of nominally 3 mm thickness.

Both the backing and bearing components are split along a line 12 which extends from their outer rims, respectively 13 and 14, to approximately the center 15 of the cup. This produces a main portion of the backing 16 which is substantially part-spherical, and two independent arms 17 and 18 which extend from main part 16. The external shape of inner bearing component 11 is also hemispherical and fits within backing 10, but the inner surface of the bearing component is only hemispherical over its main portion up to broken lines 19, from there it is relieved over its arms 20 and 21.

In order to locate this cup within the acetabular socket of the patient, projections in the form of spikes 22 are provided on the outer surface of the backing and holes 23 are formed at the end of each arm 17 and 18, through which pins or screws can be placed to hold the arms in position. Holes 23 and 24 extend through both the backing and the bearing component.

The cup is placed in a prepared acetabular socket with split line 12 extending downwardly substantially in line with foveal recess 5 so that the main loads are carried upwardly through main portion 16 of the backing and any deformation of the acetabulum can be accommodated by split line 12 between arms 17 and 18. In the arrangement shown, the cup is applied for use with a physiological bearing surface typically 40 mm to 60 mm, but the cup could be made for more normal total hip bearing diameters down to 22 mm.

The relieved surfaces on the inner bearing component allow for flexibility when cooperating with the femoral component (not shown). The main portion of the inner bearing component is spherically machined to be a very close fit with the diameter of the cooperating metal femoral component, but to avoid creating a binding fit at the bearing surface the two arms are relieved as described above.

The relieving can be done by a number of alternative geometrical configurations, for example, the same spherical radius could be chosen for the three compartments, but different centers of rotation can be chosen for each, or alternatively a larger radius could be chosen on the same center for the two arms. Again, a slightly larger radius can be used with an orbiting center of rotation to provide a relief which is tangential at the junction with the curvature of the main portion 16. It is important that there is a clearance area around the equator of the cup when the femoral component is bearing on the main portion of the cup as, for example, when walking. When unusual forces come into play, for example, when rising from a seat, then bearing can occur in the clearance area as either of the two arm portions have adequate contact area.

The molded backing is attached to the bearing portion so that the bearing portion extends somewhat to provide an undercut ridge around the rim. On the outside surface the plastics material bearing portion is roughened in order to obtain greater adhesion between the two parts. Spikes at 22 are intended to resist any sliding movement between the implant and the bone.

The preferred cup design of the present invention transfers the load into the pelvis in as physiological a way as possible so that the load is not transferred to the lower parts of the acetabulum, but is pointed directly along the lines 7 as shown in FIG. 1.

In the embodiment shown in FIGS. 3, 4, 5, 6 and 7 similar reference numerals are used to indicate similar parts. In this arrangement however, arms 17 and 18 are spaced apart to provide a gap or opening 30 between them. As will be seen, the arms are spaced apart about an arc on the part-spherical main portion 16 breaking out on rim 14, and the arms themselves and the main portion are together substantially part-spherical. The backing thus comprises a substantially part-spherical wall having a rim which is interrupted by a shaped opening to provide the two spaced apart arms 17 and 18. In fact, the rim is extended inwardly around the opening.

The main part 31 of opening 30 is substantially semicircular and has a mouth 32 which provides the interruption in the rim and which is of smaller width than the remainder 31 of the opening. The backing is therefore substantially horse-shoe shaped. The spikes 22 are provided on the backing itself but in an alternative embodiment they could be provided on the inner bearing component and extend through apertures in the backing. The backing is sufficiently flexible to accept deformation of the acetabulum of the patient, but is it usually stiffer than the inner bearing component.

It has been found that this particular shape of opening is convenient and successful and the load is transferred into the pelvis as required, in particular, this shape of opening efficiently ensures that no load is transferred onto the bone at undesired locations.

As with the arrangement shown in FIG. 1, the separate backing and the bearing component can be made from synthetic plastic material and the backing should be molded around the inner baring component. The bearing surface of the bearing component is again relieved as described with regard to FIG. 1.

Figure 8:
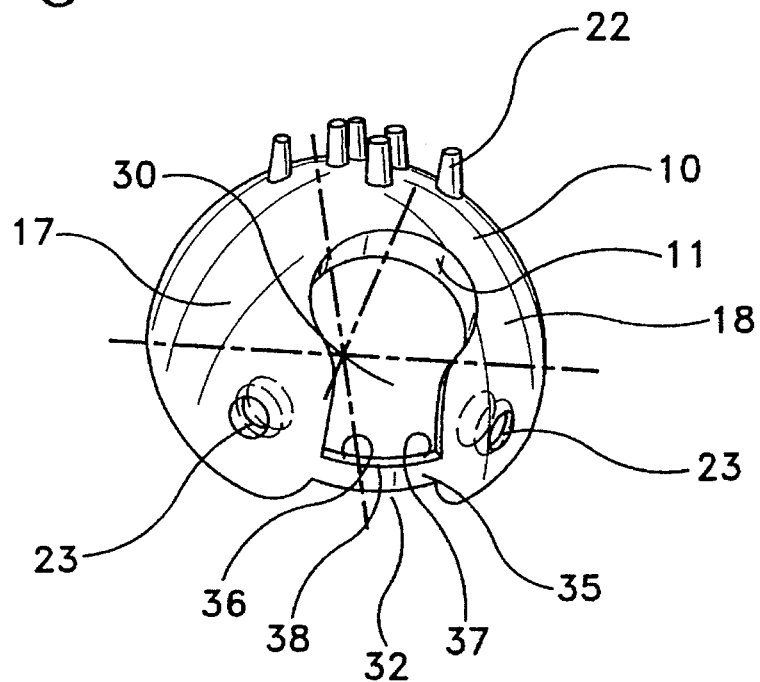
FIG. 8 is an isometric view of a modification of the construction shown in FIGS. 3 to 7.
Figure 9:
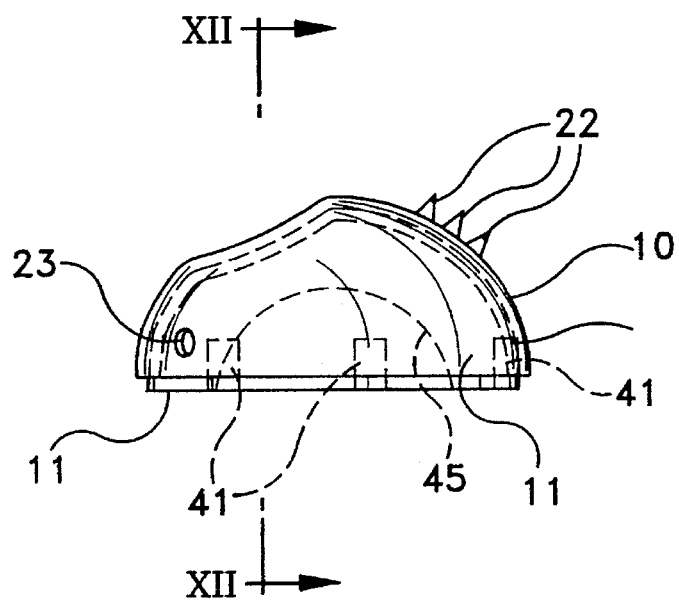
FIG. 9 is a side elevation of an alternative construction of the cup.
Figure 10:
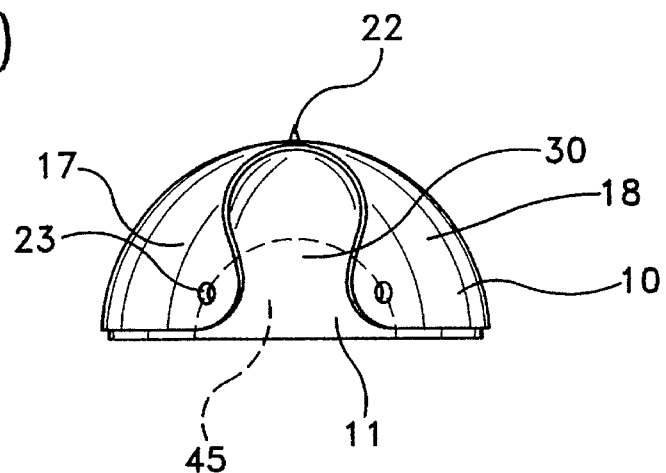
FIG. 10 is an end elevation of the cup shown in FIG. 8.
Figure 11:
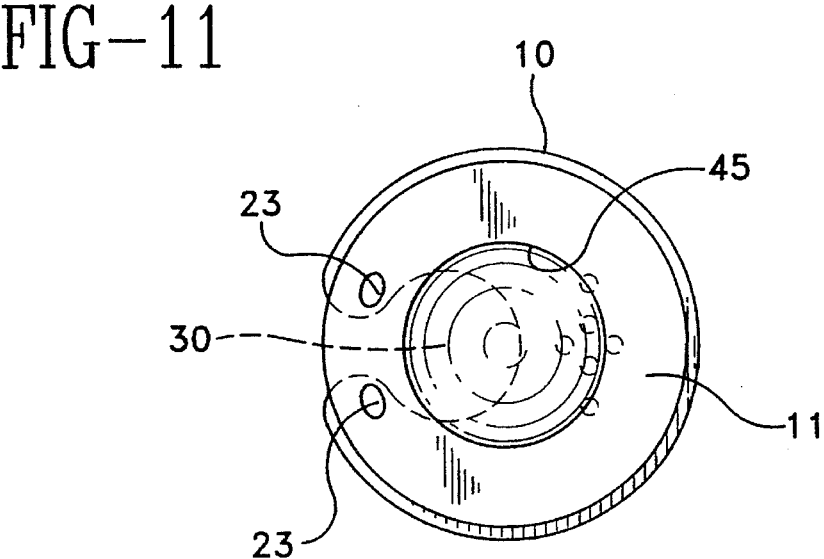
FIG. 11 is a plan view from below of the cup shown in FIGS. 9 and 10.
Figure 12:
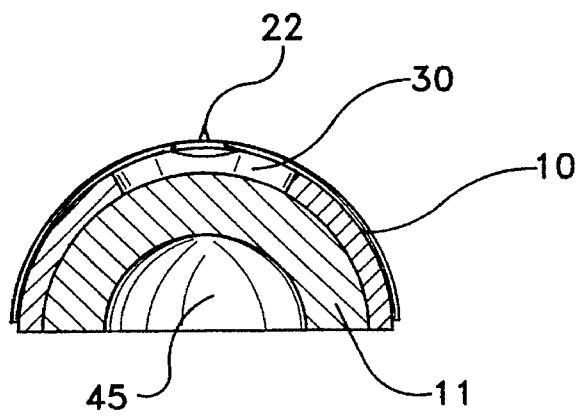
FIG. 12 is a cross-sectional end elevation taken on the line XII—XII of FIG. 9.

FIG. 8 shows a modified form of the embodiment shown in FIGS. 3, 4, 5, 6 and 7 and the same reference numerals are used to indicate similar parts. In this embodiment, to prevent collapse of the horse-shoe shaped components as it is pressed into the acetabulum, a divided spacer bar 35 is provided which bridges mouth 32 of opening 30 where the opening meets the equatorial rim of the backing. It will be seen that bar 35 comprises two extensions 36 and 37 respectively on arms 17 and 18 and the abutting ends contact each other at the line 38. By providing the bar in two parts, the arms of the horse-shoe shaped backing can deflect open, but collapse is resisted as the ends of extensions 36 and 37 come into direct abutment on the line 38.

FIGS. 9, 10, 11 and 12 show yet another embodiment which is intended for use for a more normal total hip spherical bearing or head diameter down to about 22 mm. Once again, in these figures the same reference numerals are used to indicate similar parts to those shown in FIGS. 4, 5, 6, 7 and 8. In this embodiment the inner bearing component 11 is not provided with an opening or a slot and it is substantially hemispherical, thus, the inner bearing surface 45 is unbroken. When making this type of device and molding the parts together, it is possible for the opening 30 to be filled by the material from the bearing component 11.

Load transfer is minimized or eliminated from the boss which forms within the opening by recessing the boss so it is not flush with the outer surface of the backing. Moreover, the modulus of elasticity of the bearing surface is arranged to be lower than that of the surrounding backing, and therefore the increased rigidity of the backing will cause load to be preferentially transferred to the bone through this more rigid portion. Various way of holding the backing in location in the acetabulum can be employed.

Figure 4:
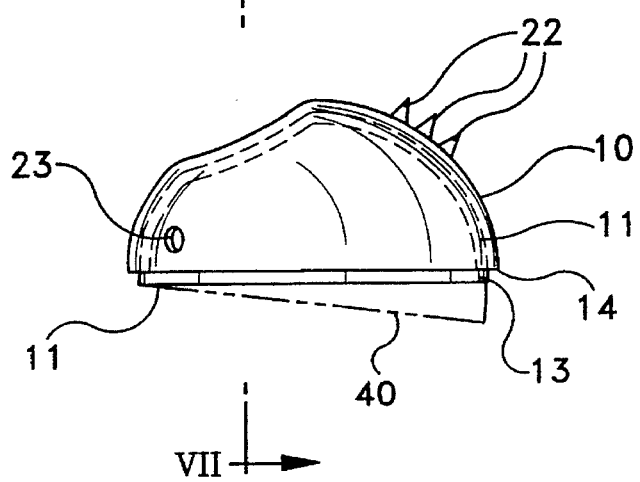
FIG. 4 is a side elevation of the acetabular cup shown in FIG. 3.
Figure 5:
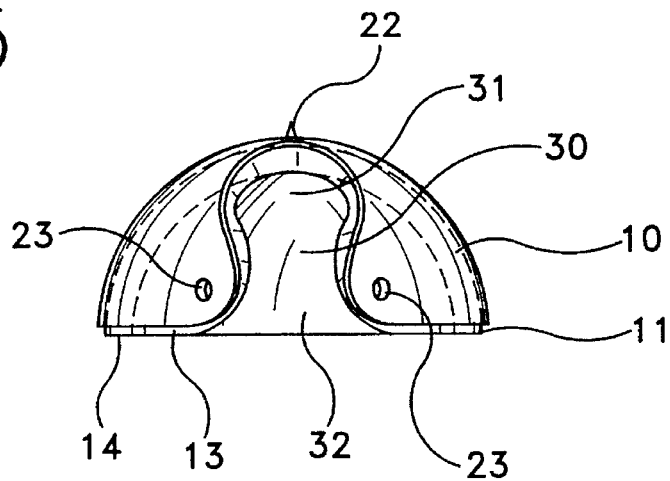
FIG. 5 is an end elevation of the cup shown in FIG. 3.
Figure 6:
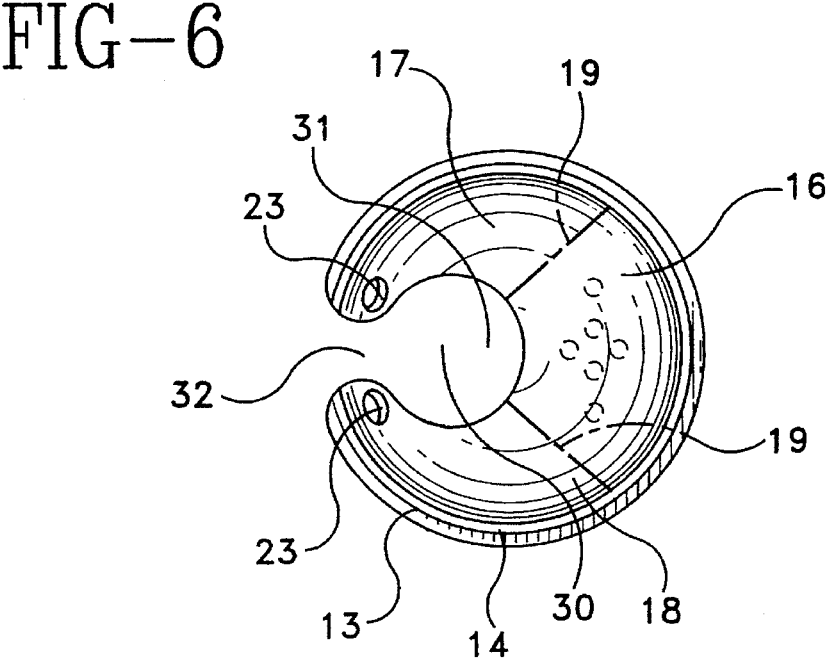
FIG. 6 is a plan view from below the cup shown in FIGS. 3, 4 and 5.
Figure 7:
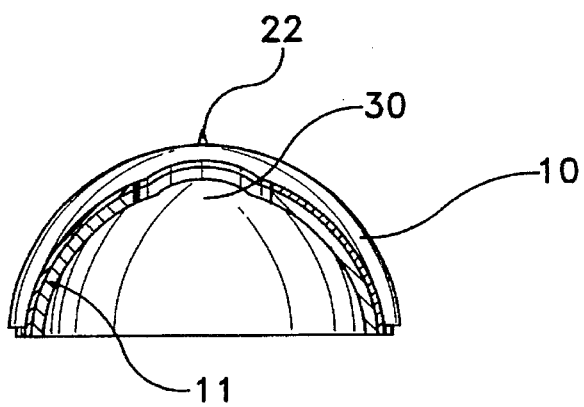
FIG. 7 is a cross-sectional view of the line VII—VII of FIG. 4.

A hood or skirt could be provided on an optional bearing insert and such a feature is indicated by broken lines 40 in FIG. 4. Bearing inserts carrying such features are known in themselves and are shown, for example, in FIG. 32 of U.S. Pat. No. 4,678,472. As such constructions are known, they will not be described herein in further detail.

While several examples of the present invention have been described, it is obvious that many changes and modifications may be made thereunto, without departing from the spirit and scope of the invention.

We claim:

1. An acetabular cup for a total hip prosthesis comprising:

an inner bearing component; and an outer shell mechanically coupled to said inner bearing component, said shell having been formed from chopped carbon fiber reinforced plastic by molding around the inner bearing component and having an elastic modulus similar to subchondral bone of between 5.6 GPa and 18.6 GPa, with said inner bearing component having a lower elastic modulus and said shell having a part-spherical main portion and two independent arms separated from each other and projecting from said main portion forming an opening, each of said arms terminating at end portions adjacent said opening and opposite said main portion, each of said end portions having an aperture formed therethrough for receiving a fixation means to fix said arms to the natural acetabulum and a plurality of spikes extending from said main portion of said shell on a portion thereof adjacent to a central portion of said opening.

2. The acetabular cup as set forth in claim 1 wherein said inner bearing component has a generally hemispherical shape.

3. The acetabular cup as set forth in claim 1 wherein said shell has a rim adjacent an equator of the part-spherical main portion and said arms are spaced apart from each other about an arc on the part-spherical shell with said end portions adjacent the rim.

4. The acetabular cup as set forth in claim 3 wherein said main portion and said arms are both substantially part-spherical.

5. The acetabular cup as set forth in claim 3 wherein the opening is semicircular.

6. The acetabular up as set forth in claim 5 wherein the opening has a mouth which provides said interruption in the rim, wherein said mouth is of smaller width than the remainder of said opening.

7. The acetabular cup as set forth in claim 3 wherein said shell is substantially horse-shoe shaped.

8. The acetabular cup as set forth in claim 1 wherein the fixation means are screws, pins, pegs or dowels.

9. The acetabular cup as set forth in claim 1 wherein the inner bearing component has an inner bearing surface having a first portion spaced diametrically opposite the separation between the arms of said shell when located therein which is part spherical and a second portion which is relieved with respect to said first portion.

10. The acetabular cup as set forth in claim 9 in which the relief of said second portion forms a tangent with said first part-spherical portion.

11. The acetabular cup as set forth in claim 1 wherein said bearing component is of substantially the same configuration as said shell.

12. The acetabular cup as set forth in claim 1 wherein the inner bearing component is rigidly secured to the shell.

* * * * *